US005618935A

United States Patent [19]

Shoshi et al.

[11] Patent Number: 5,618,935

[45] Date of Patent: Apr. 8, 1997

[54] TRICYCLIC PYRAZINE COMPOUND AND ELECTROPHOTOGRAPHIC PHOTOCONDUCTOR COMPRISING THE SAME

[75] Inventors: Masayuki Shoshi; Yumi Ichikawa, both of Yokohama; Kaoru Teramura, Kawasaki; Masayuki Koyano, Sagamihara; Megumi Kawahara, Yokohama, all of Japan

[73] Assignee: Ricoh Company, Ltd., Tokyo, Japan

[21] Appl. No.: 409,722

[22] Filed: Mar. 24, 1995

Related U.S. Application Data

[62] Division of Ser. No. 261,265, Jun. 15, 1994, Pat. No. 5,460,909.

[30] Foreign Application Priority Data

Jun. 15, 1993 [JP] Japan .................................... 5-168512

[51] Int. Cl.$^6$ ........................ C07D 241/36; G03G 5/047; G03G 5/09

[52] U.S. Cl. ............................................................. 544/344

[58] Field of Search .............................................. 544/344

[56] References Cited

PUBLICATIONS

Grigg Zet. Letters 31, 7215 (1990).

*Primary Examiner*—Mark L. Berch

*Attorney, Agent, or Firm*—Oblon, Spivak, McClelland, Maier & Neustadt, P.C.

[57] ABSTRACT

A pyrazine compound of formula (I) and a pyrazine compound of formula (II):

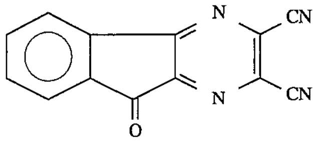

(I)

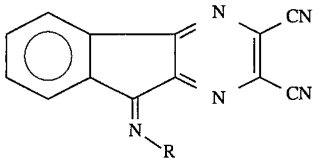

(II)

wherein R is an unsubstituted or substituted phenyl group, an unsubstituted or substituted naphthyl group; and an electrophotographic photoconductor which includes an electroconductive support and a photoconductive layer formed thereon containing a charge generating material and a charge transporting material which is any of the above-mentioned pyrazine compounds of formula (I) and formula (II).

2 Claims, 3 Drawing Sheets

TRICYCLIC PYRAZINE COMPOUND AND ELECTROPHOTOGRAPHIC PHOTOCONDUCTOR COMPRISING THE SAME

This is a Division, of application Ser. No. 08/261,265 filed on Jun. 15, 1994 now U.S. Pat. No. 5,460,909.

BACKGROUND OF THE INVENTION

1. Field of the Invention

The present invention relates to a pyrazine compound which is useful as a charge transporting material for an electrophotographic photoconductor, and also relates to an electrophotographic photoconductor comprising the pyrazine compound as a charge transporting material.

2. Discussion of Background

Conventionally inorganic photoconductive materials such as selenium, selenium-tellurium alloys and zinc oxide have been used as an effective component for a photoconductive layer of an electrophotographic photoconductor. Recently, however, electrophotographic photoconductors employing organic photoconductive materials have been studied and developed, and some of them are now used in practice. Most of such organic photoconductors now used in practice are of a so-called function-separated layered type comprising a charge generation layer and a charge transport layer which are overlaid. These organic photoconductors are much more improved with respect to the photosensitivity and the life thereof in comparison with conventional inorganic photoconductors, and therefore the development activities concerning such organic photoconductors are actively made from the viewpoints of the advantages thereof that they are inexpensive, safe for use in practice and have varieties of properties.

Such a layered electrophotographic photoconductor generally comprises an electroconductive support, a charge generation layer formed thereon comprising a charge generating material such as a pigment or dye, an a charge transport layer formed on the charge generation layer, comprising a charge transporting material such as hydrazone or pyrazoline. Such a charge transporting material has electron donating properties, so that a layered electrophotographic photoconductor using such a charge transporting material is of a positive-hole moving type and therefore exhibits photosensitivity when negatively charged. However, corona discharging used in such negative charging is much more unstable than that used in positive charging. Furthermore, such negative charging tends to produce ozone and nitrogen oxides in an amount of about 10 times that at the time of positive charging, and also tends to cause chemical and physical deterioration in the surface of the photoconductor because of the adsorption of the produced ozone and nitrogen oxides on the surface thereof, thus causing environmental pollution problems as well.

Furthermore, a positive charging toner is required for the development of latent electrostatic images formed on the negative charging photoconductor. However, the production of a positive charging toner is difficult in view of the triboelectrical charging series thereof with respect to ferromagnetic carrier particles to be used in combination with the toner.

In addition, in a two-component, high resistivity magnetic brush development method, a developer comprising a negative charging toner is much more stable and has more freedom in the formulation design thereof than the developer comprising a positive charging toner. Also from this point of view, a positive charging photoconductor is more practical and has a wider application scope than the negative charging photoconductor.

Under such circumstances, the use of a photoconductor comprising an organic photoconductive material under positive charging has been proposed.

When an organic electrophotographic photoconductor is fabricated by overlaying a charge transport layer on a charge generation layer, for example, 2,4,7-trinitro-9-fluorenone is employed as a charge transporting material for the charge transport layer since it has a great charge transporting performance. However, this material is carcinogenic and therefore extremely unsuitable for use in practice in view of industrial hygiene.

U.S. Pat. No. 3,615,414 discloses a positive charging photoconductor which comprises a thiapyrylium salt serving as a charge generating material and polycarbonate serving as a binder agent which constitute a eutectic crystal complex. This photoconductor, however, has the shortcomings that considerable memory development takes place and ghost images are formed quite easily.

In order to eliminate the above-mentioned shortcomings, a layered photoconductor for positive charging may be proposed, which comprises an upper surface layer serving as a charge generation layer comprising a charge generating material which is capable of generating positive holes and electrons, and a lower layer serving as a charge transport layer comprising a charge transporting material which has a positive-hole-transporting performance. This layered photoconductor, however, has the shortcomings that the electrophotographic performance deteriorates in the course of the preservation of the photoconductor and also in the course of image formation, thus producing images with low image density. This is because the layer comprising the charge generating material is situated on the top of the photoconductor and therefore the charge generating material which is weak and susceptible to external actions, for example, coherent light beam radiation, such as ultraviolet light radiation, corona discharging, humidity, and mechanical frictions, is easily affected by such external actions.

In the conventional photoconductor for negative charging provided with the charge transport layer as the top layer thereof, the photoconductor is rarely affected by the above-mentioned external actions, and the charge transport layer rather serves to protect the inner charge generation layer.

For the protection of the charge generation layer, a protective layer made of an insulating and transparent resin may be proposed. However, such a protective layer may block the electrons generated when the charge generation layer is radiated, so that the radiation effect is redued, and when the protective layer is thick, the photosensitivity of the photoconductor is significantly decreased.

Under such circumstances, various trials have been made and now are being made to obtain a photoconductor for use with positive charging. However, photoconductors proposed so far have various problems to be solved, in particular, with respect to photosensitivity, memory development phenomenon and industrial hygiene.

SUMMARY OF THE INVENTION

It is therefore a first object of the present invention to provide a novel pyrazine compound which is useful as a charge transporting material for use in electrophotographic photoconductors.

A second object of the present invention is to provide an electrophotographic photoconductor with high photosensitivity and high durability, which comprises an electroconductive support and a photoconductive layer formed thereon comprising a charge generating material and a charge transporting material comprising the above-mentioned pyrazine compound.

The first object of the present invention is attained by a pyrazine compound of formula (I) and a pyrazine compound of formula (II):

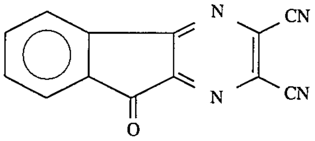
(I)

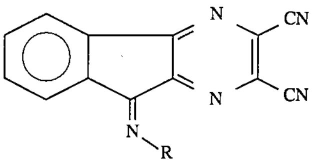
(II)

wherein R is an unsubstituted or substituted phenyl group, an unsubstituted or substituted naphthyl group.

The second object of the present invention is attained by an electrophotographic photoconductor which comprises an electroconductive support and a photoconductive layer formed thereon comprising a charge generating material and a charge transporting material comprising any of the above-mentioned pyrazine compounds of formula (I) and formula (II).

BRIEF DESCRIPTION OF THE DRAWINGS

A more complete appreciation of the invention and many of the attendant advantages thereof will readily obtained as the same becomes better understood by reference to the following detailed description when considered in connection with the accompanying drawings, wherein.

DESCRIPTION OF THE PREFERRED EMBODIMENTS

Figure 1:
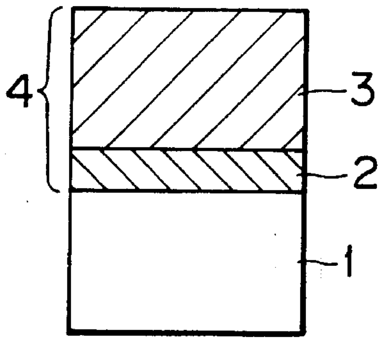
FIG. 1 is a schematic cross-sectional view of an example of an electrophotographic photoconductor according to the present invention.

As mentioned previously, the novel pyrazine compounds according to the present invention are the following pyrazine compound of formula (I) and pyrazine compound of formula (II):

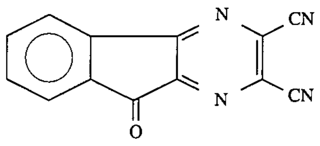
(I)

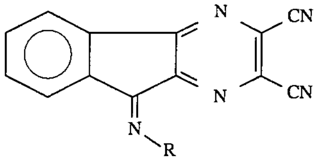
(II)

wherein R is an unsubstituted or substituted phenyl group, an unsubstituted or substituted naphthyl group.

Specific examples of the substituents of the phenyl group or naphthyl group represented by R include an alkoxyl group such as methoxy group and ethoxy group; an alkyl group such as methyl group, ethyl group, propyl group, isopropyl group, butyl group and t-butyl group; a halogen atom such as fluorine atom, chlorine atom and bromine atom; a halogenated alkyl group such as trifluoromethyl group; an alkoxycarbonyl group such as methoxycarbonyl group, and ethoxycarbonyl group; a cyano group; and a nitro group.

Specific example of the pyrazine compound of formula (II) are shown in the following TABLE 1. The pyrazine compound of formula (II) of the present invention is not limited to the pyrazine compounds shown in TABLE 1.

TABLE 1

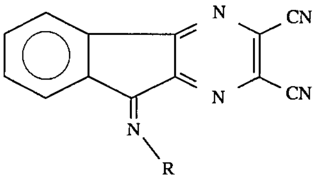

| Pyrazine Compound No. | R |
|---|---|
| II-1 | 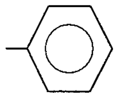 |
| II-2 | 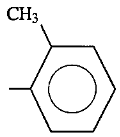 |
| II-3 | 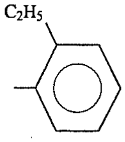 |
| II-4 | 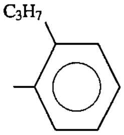 |

TABLE 1-continued
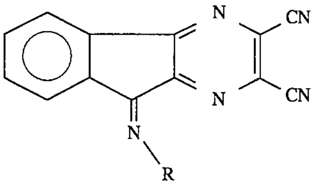
| Pyrazine Compound No. | R |
|---|---|
| II-5 | 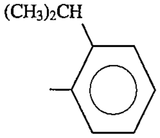 |
| II-6 | 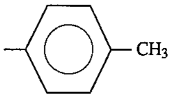 |
| II-7 | 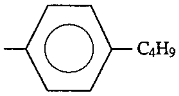 |
| II-8 | 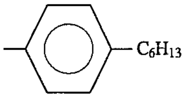 |
| II-9 | 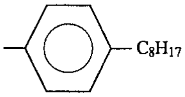 |
| II-10 | 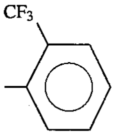 |
| II-11 | 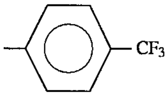 |
| II-12 | 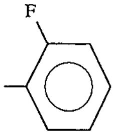 |
| II-13 | 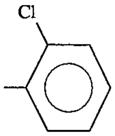 |
| II-14 | 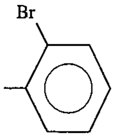 |
TABLE 1-continued
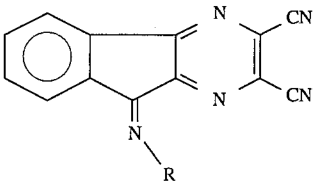
| Pyrazine Compound No. | R |
|---|---|
| II-15 | 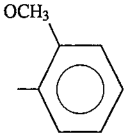 |
| II-16 | 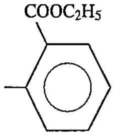 |
| II-17 | 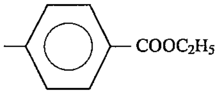 |
| II-18 | 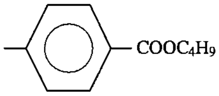 |
| II-19 | 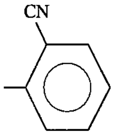 |
| II-20 | 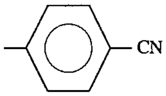 |
| II-21 | 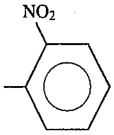 |
| II-22 | 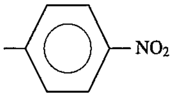 |
| II-23 | 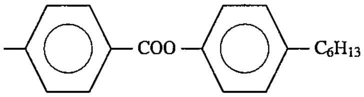 |
| II-24 | 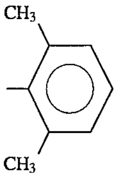 |

TABLE 1-continued
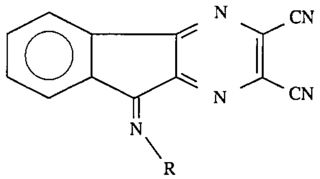
| Pyrazine Compound No. | R |
|---|---|
| II-25 | 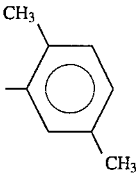 |
| II-26 | 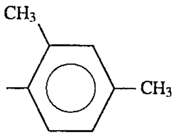 |
| II-27 | 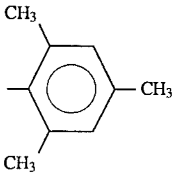 |
| II-28 | 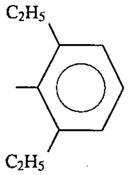 |
| II-29 | 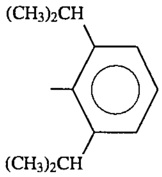 |
| II-30 | 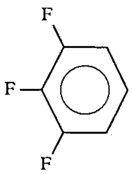 |
| II-31 | 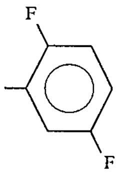 |
TABLE 1-continued
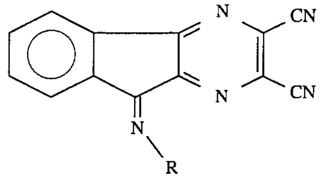
| Pyrazine Compound No. | R |
|---|---|
| II-32 | 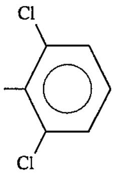 |
| II-33 | 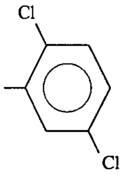 |
| II-34 | 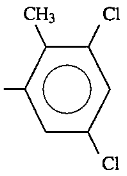 |
| II-35 | 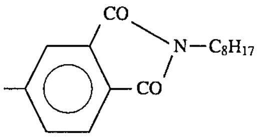 |
| II-36 | 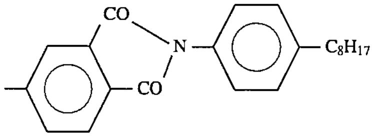 |
| II-37 | 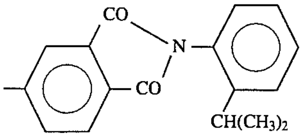 |
| II-38 | 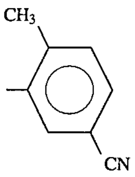 |
| II-39 | 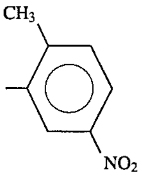 |

TABLE 1-continued

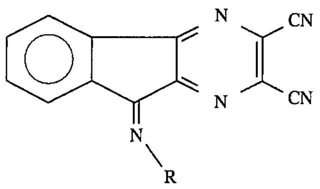

| Pyrazine Compound No. | R |
|---|---|
| II-40 | 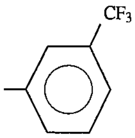 |
| II-41 | 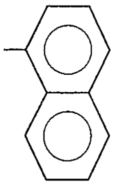 |
| II-42 | 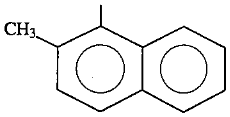 |
| II-43 | 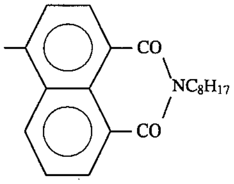 |
| II-44 | 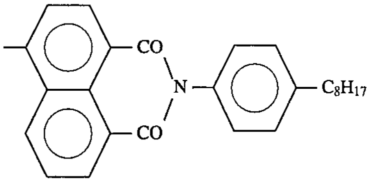 |
| II-45 | 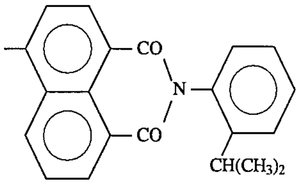 |
| II-46 | 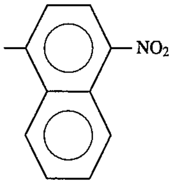 |

The pyrazine compound of formula (I) and the pyrazine compound of formula (II) of the present invention are prepared in accordance with the following reaction scheme:

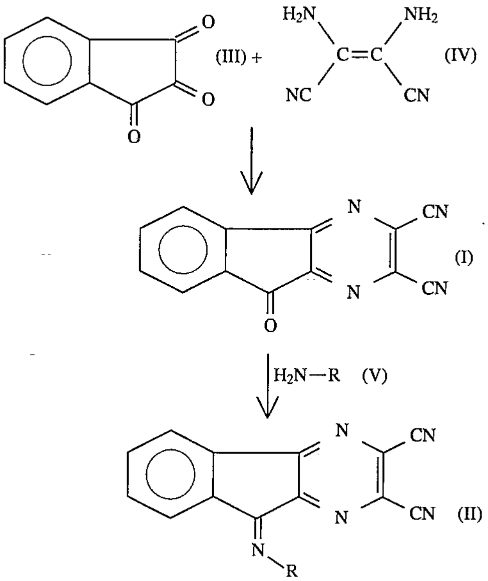

More specifically, the pyrazine compound of formula (I) can be obtained by allowing a ninhydrin compound of formula (III) to react with a 1,2-diamino-1,2-dicyanoetheylene compound (III) with the application of heat thereto.

The above reaction can be carried out either without using any solvents or in the presence of a polar solvent such as methanol, ethanol, isopropanol, butanol, acetic acid, tetrahydrofuran, 1,4-dioxane or N,N-dimethylformamide, or in an aromatic solvent such as benzene, toluene, chlorobenzene or xylene.

The reaction temperature for the above reaction is generally in the range of room temperature to 150° C., preferably in the range of room temperature to 100° C.

Furthermore, the pyrazine compound of formula (II) can be obtained by allowing the pyrazine compound (I) to react with an amine compound of formula (V) in the presence of an acidic catalyst. Examples of the acidic catalyst for use in this reaction include organic acids such as acetic acid, trifluoroacetic acid, and trifluoroborate; and acidic inorganic materials such as zinc chloride, iron chloride, titanium tetrachloride, and aluminum chloride.

The reaction is usually carried out either without using any solvent or in the presence of a halogen solvent such as dichloromethane, chloroform or 1,2-dichloroethane; carbon disulfide; or an aromatic solvent such as chlorobenzene or nitrobenzene.

The reaction temperature for the above reaction is generally in the range of room temperature to 150° C., preferably in the range of room temperature to 100° C.

The pyrazine compounds of the present invention can be used not only as a charge transporting material for the electrophotographic photoconductor, but also as an effective material in electron devices such as a solar battery and organic EL devices in the field of electronics.

The electrophotographic photoconductor according to the present invention will now be explained with reference to the accompanying drawings.

An example of the electrophotographic photoconductor of the present invention is shown in FIG. 1, which comprises a support 1, which may be an electroconductive support, or a sheet provided with an electroconductive layer thereon, a charge generation layer 2 formed on the support 1, comprising a charge generating material and, when necessary, with the addition of a binder resin thereto, and a charge transport layer 3 formed on the charge generation layer 2, which comprises a charge transporting material comprising the pyrazine compound of formula (I) or (II) and, when necessary, with the addition of a binder resin thereto. The charge generation layer 2 and the charge transport layer 3 constitute a photoconductive layer 4 of this electrophotographic photoconductor as shown in FIG. 1.

Figure 2:
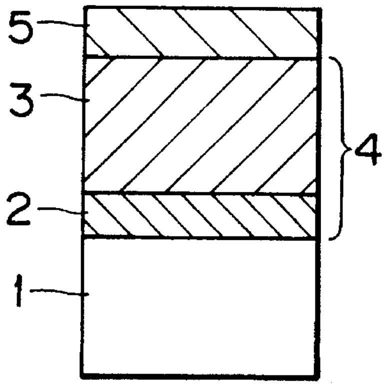
FIG. 2 is a schematic cross-sectional view of another example of an electrophotographic photoconductor according to the present invention.

FIG. 2 shows another example of the electrophotographic photoconductor, which comprises the same photoconductive layer 4 as shown in FIG. 1 and a protective layer 5 formed on the top surface of the photoconductive layer 4.

Figure 3:
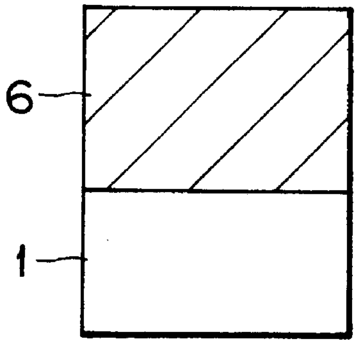
FIG. 3 is a schematic cross-sectional view of a further example of an electrophotographic photoconductor according to the present invention.

FIG. 3 shows a further example of the electrophotographic photoconductor of the present invention, which comprises the support 1 and a photoconductive layer 6 formed thereon comprising a charge generating material, a charge transporting material which comprises the pyrazine compound of formula (I) or (II), and when necessary, with the addition of a binder resin thereto.

The electrophotographic photoconductor as shown in FIG. 3 may be provided with a protective layer (not shown) on the top surface of the photoconductive layer 6, and also may be provided with an intermediate layer (not shown) between the support 1 and the photoconductive layer 6.

As the charge generating material for use in the electrophotographic photoconductor of the present invention, inorganic and organic materials can be employed as long as free charges can be generated therefrom upon absorbing visible light.

Specific examples of such a charge generating material include inorganic materials such as amorphous selenium, trigonal system selenium, selenium-arsenic alloy, selenium-tellurium alloy, cadmium sulfide, cadmium selenide, cadmium sulfoselenide, mercury sulfide, lead oxide, lead sulfide, and amorphous silicon; and organic materials such as bisazo dye, polyazo dye, triarylmethane dye, thiazine dye, oxyazine dye, xanthene dye, cyanine dye, styryl dye, pyrylium dye, quinacridone dye, indigoid dye, perylene dye, polycyclic quinone dye, benzimidazole dye, indanthrone dye, squarilium dye, anthraquinone dye, and phthalocyanine dye.

Examples of the binder resin for use in the photoconductive layer are addition polymerization resins, polyaddition resins and polycondensation resins, such as polyethylene, polypropylene, acrylic resin, methacrylic resin, vinyl chloride resin, vinyl acetate resin, epoxy resin, polyurethane resin, phenolic resin, polyester resin, alkyd resin, polycarbonate resin, silicone resin, and melamine resin, and copolymer resins containing at least two repeat units of these resins; insulating resins such as vinyl chloride-vinyl acetate copolymer, vinyl chloride-vinyl acetate-maleic anhydride copolymer; and polymeric organic semiconductors such as poly-N-vinylcarbazole.

As the electroconductive support for supporting the previously mentioned photoconductive layer, there can be employed metal plates and foils made of aluminum or nickel; plastic films on which aluminum, tin oxide or indium oxide is deposited; and paper, plastic films and drums on which an electroconductive material is coated.

The fabrication of the electrophotographic photoconductor of the present invention will now be explained.

In the case where the electrophotographic photoconductor of the present invention is of a layered type, which comprises a charge generation layer and a charge transport layer, as shown in FIG. 1 and FIG. 2, the charge generation layer 2 is first formed on an electroconductive layer.

The charge generation layer 2 may be formed by depositing in vacuum a charge generating material on the electroconductive support or by coating a coating liquid comprising a charge generating material dissolved or dispersed in an appropriate solvent, when necessary, with the addition of a binder agent thereto, on the electroconductive support 1, drying the coated liquid.

When the charge generation layer 2 is formed by using a coating liquid in which the charge generating material is dispersed in a solvent, it is preferable that the average particle size of the dispersed charge generating material be 2 μm or less, more preferably 1 μm or less.

When the particle size of the dispersed charge generating material is larger than the above-mentioned particle size, the charge generating material cannot be dispersed well and tends to stick out from the surface of the charge generation layer 2. This impairs the smoothness of the surface of the charge generation layer 2, and discharging may take place at the stuck particles of the charge generating material, or toner is deposited on such stuck particles of the charge generating material with the occurrence of the toner filming phenomenon, in particular, when the charge generation layer 2 is placed on top of the photoconductor (not shown). However, when the particle size of the dispersed charge generating material is extremely small, the particles tend to aggregate so that the resistivity of the charge generation layer 2 may be excessively increased, or the photosensitivity and repeat use durability are lowered because of the increase of crystal defects in the charge generation layer. Furthermore, there is a limitation on the pulverization of the charge generating material. For these reasons, it is preferable that the lower limit of the average particle size of the charge generating material be 0.01 μm.

The charge generation layer 2 can be provided by the following method:

A charge generating material is finely divided in a dispersant in a ball mill or homomixer. To this dispersion of the charge generating material, a binder resin is added, and the mixture is again dispersed, whereby a charge generation layer formation coating liquid can be prepared.

The charge generating material can be uniformly dispersed under the application of ultrasonic wave.

It is preferable that the amount of the charge generating material in the charge generation layer 2 be in the range of 20 to 200 parts by weight to 100 parts by weight of the binder resin in the charge generation layer 2.

It is preferable that the thickness of the thus formed charge generation layer 2 be in the range of 0.1 to 10 μm, more preferably in the range of 0.5 to 5 μm.

A charge transport layer 3 can be formed on the above formed charge generation layer 2 as follows:

A charge generating material is dissolved or dispersed in an appropriate solvent, when necessary, with the addition of an appropriate binder resin thereto, whereby a charge transport layer formation coating liquid is prepared.

The thus prepared charge transport layer formation coating liquid is then coated on the above formed charge generation layer 2 and dried, whereby a charge transport layer 3 can be formed on the charge generation layer 2.

Examples of the solvent for use in the charge transport layer formation liquid are N,N-dimethylformaldehyde, toluene, xylene, monochlorobenzene, 1,2-dichloroethane, dichloromethane, 1,1,1-trichloroethane, 1,1,2-trichloroethylene, tetrahydrofuran, methyl ethyl ketone, cyclohexanone, ethyl acetate, and butyl acetate.

It is preferable that the amount of the charge transporting material in the charge transport layer 3 be in the range of 20 to 200 parts by weight to 100 parts by weight of the binder resin in the charge transport layer 3.

It is preferable that the thickness of the thus formed charge transport layer 3 be in the range of 5 to 50 μm, more preferably in the range of 5 to 30 μm.

In the case where the electrophotographic photoconductor of the present invention is of a single layer type, as shown in FIG. 3, a photoconductive layer formation coating liquid is prepared by dissolving or dispersing the charge generating material, the charge transporting material of the present invention, and a binder agent in an appropriate solvent, and the thus prepared photoconductor layer formation coating liquid is coated on an electroconductive support 1, and dried, whereby an electrophotographic photoconductor comprising the electroconductive support 1, and a photoconductive layer 6 formed thereon which comprises the charge generating material, the charge transporting material of the present invention, and the binder resin, can be prepared as shown in FIG. 3.

It is preferable that the amount of the charge generating material and the amount of the charge transporting material in the photoconductive layer 6 be respectively in the range of 20 to 200 parts by weight and in the range of 20 to 200 parts by weight to 100 parts by weight of the binder resin contained in the photoconductive layer 6.

It is preferable that the thickness of the thus formed photoconductive layer 6 be in the range of 7 to 50 μm, more preferably in the range of 10 to 30 μm.

The previously mentioned intermediate layer, which is to be interposed between the electroconductive support 1 and the photoconductive layer 4 or 6, serves as an adhesive layer or a barrier layer as well, so that in addition to the previously mentioned binder resins, the following resins can be employed: polyvinyl alcohol, ethyl cellulose, carboxymethyl cellulose, vinyl chloride-vinyl acetate copolymer, vinyl chloride-vinyl acetate-maleic anhydride copolymer, casein, and N-alkoxymethylnylon.

Furthermore, the above-mentioned resins in which tin oxide or indium is dispersed can also be employed as the material for the intermediate layer. In addition, a layer formed by vacuum deposition of a material such as aluminum oxide, zinc oxide, or silicon oxide can also be employed as the intermediate layer.

It is preferable that the thickness of the intermediate layer be 1 μm or less.

As the material for the previously mentioned protective layer, the previously mentioned resins can be used as they are. Alternatively, the above-mentioned resins in which a low-resistivity material such as tin oxide or indium oxide is dispersed can be employed. In addition, an organic plasma polymerized film can be employed. Such an organic plasma polymerized film may contain oxygen, nitrogen, a halogen atom, and atoms in Groups III and V in the Periodic Table.

Other features of the present invention will become apparent in the course of the following description of exemplary embodiments, which are given for illustration of the invention and are not intended to be limiting thereof.

EXAMPLE 1-1

[Synthesis of Pyrazine Compound of Formula (I)]

8.91 g of ninhydrin (commercially available) and 5.41 g of 1,2-diamino-1,2-dicyanoethylene (commercially available) were added to 200 ml of isopropyl alcohol. This mixture was refluxed for 2 hours, and was then allowed to cool to room temperature.

Crystals separated from the above reaction mixture were filtered off, whereby a crude product was obtained.

The thus obtained crude crystalline product was recrystallized from toluene, whereby the pyrazine compound of formula (I), with a decomposition point of 266.5° C., was obtained in a yield of 7.16 g.

Figure 4:
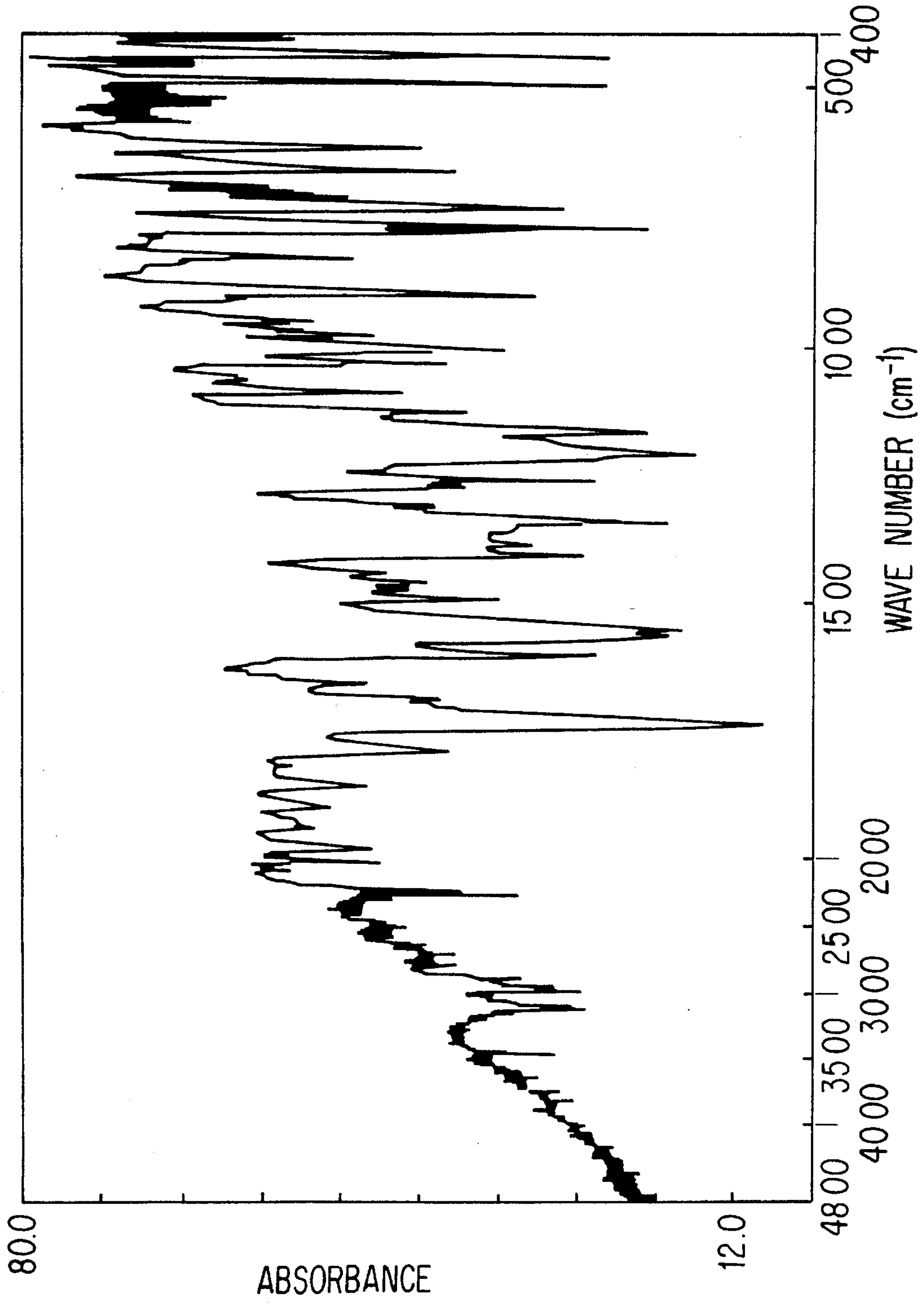
FIG. 4 is an IR transmission spectrum of a pyrazine compound of formula (I) obtained in Example 1—1.

FIG. 4 is the IR absorption spectrum of the pyrazine compound of formula (I) obtained in Example 1'-1.

EXAMPLE 1-2

[Synthesis of Pyrazine Compound No. II-5]

4.64 g of the pyrazine compound of formula (I) obtained in Example 1-1 was dissolved in 200 ml of 1,2-dichloroethane. To this mixture, 5.45 g of zinc chloride was added with stirring at room temperature, and then 5.41 g of 2-isopropyl aniline was added dropwise over a period of 10 minutes. This reaction mixture was stirred at 50° C. for 6 hours.

After the reaction, this reaction mixture was then cooled to room temperature, and was then poured into ice water. The reaction mixture was extracted with 1,2-dichloroethane, and the 1,2-dichloroethane extract layer was washed with water until the extract layer became neutral.

The 1,2-dichloroethane extract layer was then dried over anhydrous magnesium sulfate and the 1,2-dichloroethane was distilled away. The residue was subjected to column chromatography and was eluted with 1,2-dichloroethane, whereby a crude product was obtained.

The thus obtained crude product was recrystallized from n-butanol, whereby pyrazine compound No. II-5 in TABLE 1, with a melting point of 188.8° to 189.7° C., was obtained in a yield of 2.09 g.

Figure 5:
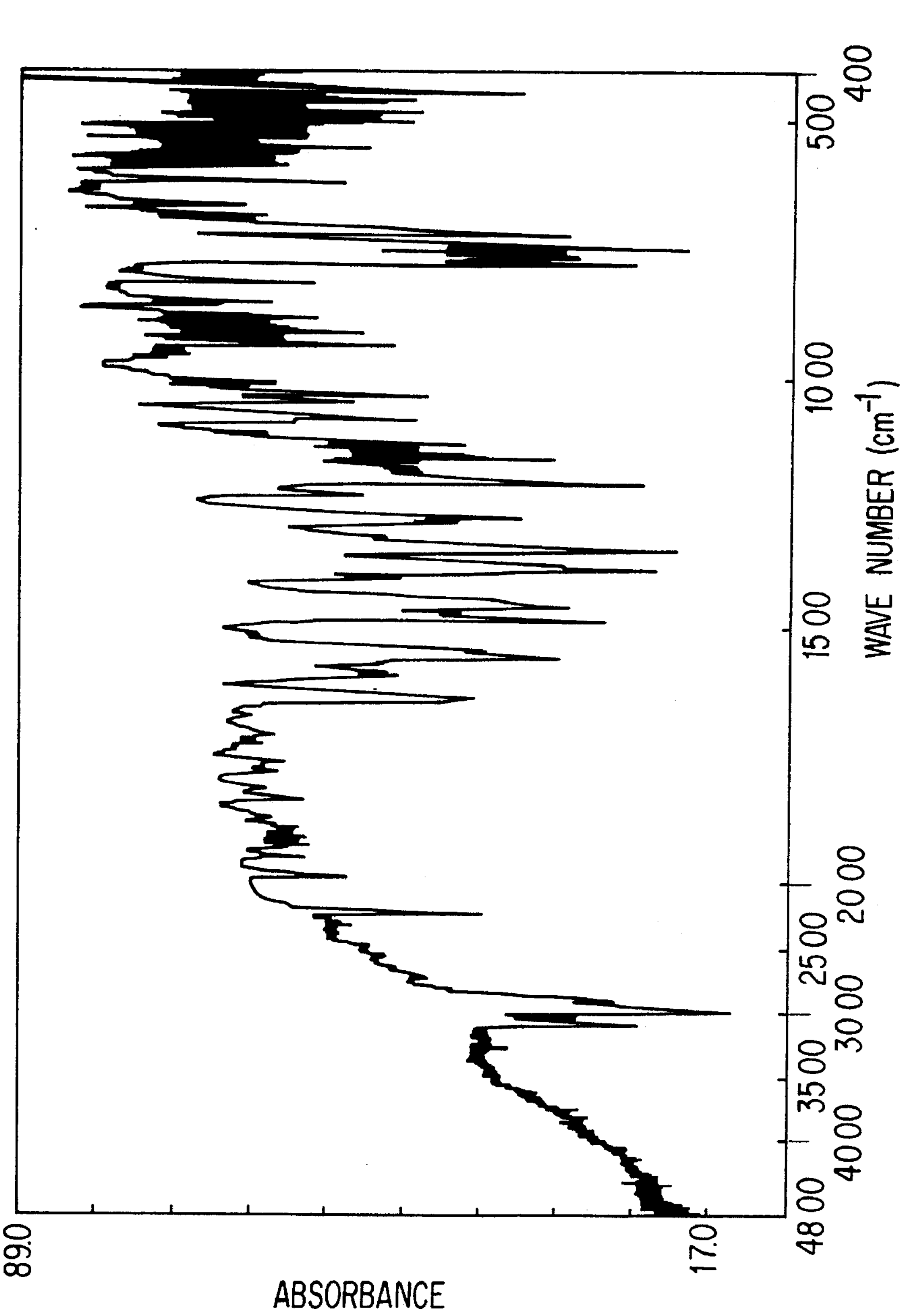
FIG. 5 is an IR transmission spectrum of a pyrazine compound No. II-5 in TABLE 1 obtained in Example 1-2.

FIG. 5 is the IR absorption spectrum of the pyrazine compound No. II-5 obtained in Example 1-2.

EXAMPLES 1-3 to 1-6

[Synthesis of Pyrazine Compounds of Formula (II)]

The procedure for synthesizing the pyrazine compound of formula (II) was repeated except that the 2-isopropyl aniline employed in Example 1-2 was a variety of amines, whereby pyrazine compounds Nos. II-10, II-24, II-28 and II-41 in TABLE 1 were respectively synthesized.

The melting point and the results of the elemental analysis of each of the pyrazine compounds obtained in Examples 1-1 to 1-6 are shown in the TABLE 2:

TABLE 2

| | | | Elemental Analysis | | |
|---|---|---|---|---|---|
| Example | Pyrazine Comp. No. | Melting Point (°C.) | % C Found (Calcd.) | % H Found (Calcd.) | % N Found (Calcd.) |
| 1-1 | (1) | 266.5 (decomposed) | 67.44 (67.24) | 1.85 (1.74) | 24.16 (24.13) |
| 1-2 | II-5 | 188.5–189.7 | 75.70 (75.63) | 4.21 (4.33) | 20.08 (20.05) |
| 1-3 | II-10 | 219.5–220.2 | 64.12 (64.01) | 2.01 (2.15) | 18.59 (18.66) |
| 1-4 | II-24 | 249.5–250.0 | 75.35 (75.21) | 3.79 (3.91) | 20.86 (20.88) |
| 1-5 | II-28 | 170.5–171.5 | 75.95 (76.01) | 4.81 (4.72) | 19.22 (19.27) |
| 1-6 | II-41 | 131.0–132.0 | 77.20 (77.30) | 3.22 (3.10) | 19.67 (19.60) |

EXAMPLE 2-1

5 parts by weight of the bisazo dye of the following formula (VI) serving as a charge generating material, 2.5 parts by weight of a butyral resin (Trademark "Denka Butyral Resin #3000-2" made by Denki Kagaku Kogyo Kabushiki Kaisha) and 92.5 parts by weight of tetrahydrofuran were dispersed in a ball mill for 12 hours:

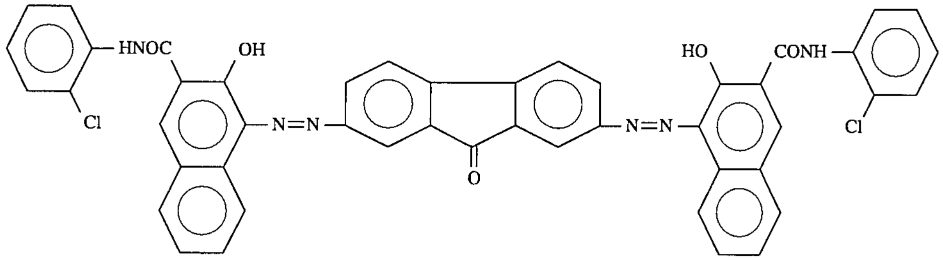
(VI)

Thereafter, tetrahydrofuran was further added to the above mixture until the above mixture became a dispersion liquid with a 2 wt.% dispersion concentration, and this mixture was dispersed again to prepare a coating liquid.

The thus prepared coating liquid was coated on an aluminum surface of an aluminum-deposited polyester film with a thickness of 100 μm serving as an electroconductive substrate by a doctor blade, and dried, whereby a charge generation layer with a thickness of 1.0 μm was formed on the aluminum-deposited polyester film.

A charge transport layer coating liquid was prepared by mixing 6 parts by weight of the pyrazine compound No. II-5 in TABLE 1, serving as a charge transporting material, 10 parts by weight of a commercially available polycarbonate resin (Trademark "K-1300" made by Teijin Chemicals, Ltd.), 0.002 parts by weight of a commercially available methylphenyl silicone (Trademark "KF50–100 cps made by Shin-Etsu Chemical Co., Ltd.) and 94 parts by weight of tetrahydrofuran.

The thus prepared charge transport layer coating liquid was coated on the above prepared charge generation layer by a doctor blade and then dried, whereby a charge transport layer with a thickness of 20.0 μm was formed on the charge generation layer, whereby an electrophotographic photoconductor No. 1 with a layered structure of aluminum electrode/charge generation layer/charge transport layer of the present invention was fabricated.

EXAMPLES 2-2 to 2-5

The procedure for fabrication of the electrophotographic photoconductor No. 1 of the present invention in Example 2-1 was repeated except that the pyrazine compound No. II-5 in TABLE 1 employed as a charge transporting material in Example 2-1 was replaced by pyrazine compound No. II-10, pyrazine compound No. II-24 , pyrazine compound No, II-28, and pyrazine compound No. II-41 in TABLE 1, respectively, whereby electrophotographic photoconductor Nos. 2, 3, 4 and 5 of the present invention were fabricated.

EXAMPLES 2-6

The procedure for preparation of the charge generation layer of the electrophotographic photoconductor No. 1 of the present invention in Example 2-1 was repeated except that 5 parts by weight of the bisazo dye employed in Example 2-1 was replaced by 6 parts by weight of the following trisazo dye of formula (VII), whereby a charge generation layer was formed on the aluminum-deposited polyester film serving as the electroconductive support:

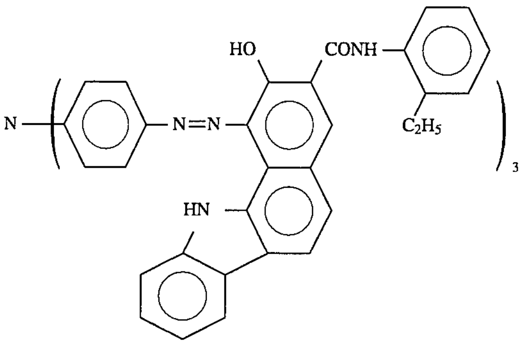
(VII)

A charge transport layer coating liquid was prepared by mixing 6 parts by weight of pyrazine compound No. II-5 in TABLE 1, serving as a charge transporting material, 10 parts by weight of a commercially available polycarbonate resin (Trademark "K-1300" made by Teijin Chemicals, Ltd.), 0.002 parts by weight of a commercially available methylphenyl silicone (Trademark "KF50–100 cps made by Shin-Etsu Chemical Co., Ltd.) and 94 parts by weight of tetrahydrofuran.

The thus prepared charge transport layer coating liquid was coated on the above prepared charge generation layer by a doctor blade and then dried, whereby a charge transport layer with a thickness of 20.0 μm was formed on the charge generation layer, whereby an electrophotographic photoconductor No. 6 with a layered structure of aluminum electrode/charge generation layer/charge transport layer of the present invention was fabricated.

EXAMPLES 2-7 to 2-10

The procedure for fabrication of the electrophotographic photoconductor No. 6 of the present invention in Example 2-was repeated except that pyrazine compound No. II-5 in TABLE 1 employed as a charge transporting material in Example 2-6 was replaced by pyrazine compound No. II-10, pyrazine compound No. II-24, pyrazine compound No. II-28, and pyrazine compound No. II-41 in TABLE 1, respectively whereby electrophotographic photoconductor Nos. 7, 8, 9 and 10 of the present invention were fabricated.

EXAMPLE 2-11

5 parts by weight of titanyl phthalocyanine serving as a charge generating material, 5 parts by weight of a polyvinyl butyral resin (Trademark "S-Lec BLS" made by Sekisui Chemical CO., Ltd.) and 90 parts by weight of tetrahydrofuran were dispersed in a ball mill for 12 hours.

Thereafter, tetrahydrofuran was further added to the above mixture until the above mixture became a dispersion liquid with a 2 wt.% dispersion concentration, and this mixture was dispersed again to prepare a coating liquid.

The thus prepared coating liquid was coated on an aluminum surface of an aluminum-deposited polyester film with a thickness of 100 μm serving as an electroconductive substrate by a doctor blade, and dried, whereby a charge generation layer with a thickness of 0.5 μm was formed on the aluminum-deposited polyester film.

A charge transport layer coating liquid was prepared by mixing 6 parts by weight of pyrazine compound No. II-5 in TABLE 1, serving as a charge transporting material, 10 parts by weight of a commercially available polycarbonate resin (Trademark "K-1300" made by Teijin Chemicals, Ltd.), and 94 parts by weight of tetrahydrofuran.

The thus prepared charge transport layer coating liquid was coated on the above prepared charge generation layer by a doctor blade and then dried, whereby a charge transport layer with a thickness of 20.0 μm was formed on the charge generation layer, whereby an electrophotographic photoconductor No. 11 with a layered structure of aluminum electrode/charge generation layer/charge transport layer of the present invention was fabricated.

EXAMPLES 2-12 TO 2-15

The procedure for fabrication of the electrophotographic photoconductor No. 11 of the present invention in Example 2-11 was repeated except that pyrazine compound No. II-5 in TABLE 1 employed as a charge transporting material in Example 2-11 was replaced by pyrazine compound No. II-10, pyrazine compound No. II-24, pyrazine compound No. II-28, and pyrazine compound No. II-41 in TABLE 1, respectively, whereby electrophotographic photoconductor Nos. 12, 13, 14 and 15 of the present invention were fabricated.

Each of the thus fabricated electrophotographic photoconductors Nos. 1 to 15 according to the present invention was charged under application of +6 kV of corona charge for 20 seconds, by use of a commercially available electrostatic copying sheet testing apparatus ("Paper Analyzer Model SP-428" made by Kawaguchi Electro Works Co., Ltd.). Then each electrophotographic photoconductor was allowed to stand in the dark for 20 seconds without applying any charges thereto, and the surface potential Vo (V) of the photoconductor was measured.

Each photoconductor was then illuminated by a tungsten lamp in such a manner that the illuminance on the illuminated surface of the photoconductor was 40 lux, and the exposure $E_{1/2}$ (lux-sec) required to reduce the initial surface potential Vo (V) to ½ thereof was measured. The results are shown in TABLE 3.

TABLE 3

| Ex. No. | Photo-conductor | CGM | Pyrazine Compound No. | Vo(V) | $E_{1/2}$ (lux · sec) |
|---|---|---|---|---|---|
| 2-1 | 1 | (A) | II-5 | 1906 | 14.2 |
| 2-2 | 2 | (A) | II-10 | 1298 | 32.9 |
| 2-3 | 3 | (A) | II-24 | 1678 | 30.5 |
| 2-4 | 4 | (A) | II-28 | 1937 | 15.1 |
| 2-5 | 5 | (A) | II-41 | 1832 | 21.6 |
| 2-6 | 6 | (B) | II-5 | 1316 | 10.7 |
| 2-7 | 7 | (B) | II-10 | 1229 | 26.6 |
| 2-8 | 8 | (B) | II-24 | 1417 | 27.4 |
| 2-9 | 9 | (B) | II-28 | 1255 | 5.3 |
| 2-10 | 10 | (B) | II-41 | 1079 | 11.9 |
| 2-11 | 11 | (C) | II-5 | 1206 | 8.1 |
| 2-12 | 12 | (C) | II-10 | 1459 | 14.6 |
| 2-13 | 13 | (C) | II-24 | 1558 | 23.8 |
| 2-14 | 14 | (C) | II-28 | 1209 | 5.9 |
| 2-15 | 15 | (C) | II-41 | 1165 | 10.1 |

(A): Bisazo dye of formula (VI)
(B): Trisazo dye of formula (VII)
(C): Titanyl phthalocyanine The pyrazine compound of formula (I) and pyrazine compounds of general formula (II) are novel and can be produced easily with high yields.

These compounds exhibit excellent solubility or dispersibility in binder resins and are charge transporting materials with excellent charge transporting performance, which accept electric charges generated from charge generating materials and transport the same.

The electrophotographic photoconductors of the present invention which employ these pyrazine compounds as charge transporting materials exhibit high photosensitivity and durability.

Japanese Patent Application No. 05-168512 filed on Jun. 15, 1993, (See U.S. Pat. No. 5,460,909) is hereby incorporated by reference.

What is claimed is:

1. A pyrazine compound of formula (II):

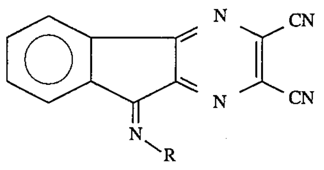

wherein R is a phenyl group which may have a substituent, or a naphthyl group which may have a substituent, wherein said substituent on each of the phenyl and naphthyl groups is selected from the group consisting of alkoxyl, alkyl, halogen, halogenated alkyl, alkoxycarbonyl, cyano and nitro.

2. The pyrazine compound of claim 1, wherein said alkoxy group is methoxy or ethoxy, said alkyl group is methyl, ethyl, propyl, isopropyl, butyl or t-butyl, said halogen is fluorine, chlorine or bromine, said halogenated alkyl is trifluoromethyl and said alkoxycarbonyl group is methoxycarbonyl or ethoxycarbonyl.

* * * * *